US008865955B2

(12) United States Patent
Krupa et al.

(10) Patent No.: US 8,865,955 B2
(45) Date of Patent: Oct. 21, 2014

(54) PROCESS AND APPARATUS FOR OLIGOMERIZING ONE OR MORE HYDROCARBONS

(75) Inventors: Steven Lee Krupa, Fox River Grove, IL (US); Christian D. Freet, South Elgin, IL (US); Mohamed Shakur, Hoffman Estates, IL (US)

(73) Assignee: UOP LLC, Des Plaines, IL (US)

( * ) Notice: Subject to any disclaimer, the term of this patent is extended or adjusted under 35 U.S.C. 154(b) by 482 days.

(21) Appl. No.: 12/965,425

(22) Filed: Dec. 10, 2010

(65) Prior Publication Data

US 2012/0149956 A1 Jun. 14, 2012

(51) Int. Cl.
$C07C\ 2/08$ (2006.01)
$C07C\ 2/18$ (2006.01)

(52) U.S. Cl.
CPC ............ $C07C\ 2/18$ (2013.01); $C07C\ 2527/173$ (2013.01)
USPC ........... 585/302; 585/303; 585/510; 585/514; 585/515; 585/518; 585/520; 585/526; 585/527; 585/529

(58) Field of Classification Search
USPC ......... 585/304, 502, 510, 514, 515, 520, 526, 585/527, 529, 518, 302, 303
See application file for complete search history.

(56) References Cited

U.S. PATENT DOCUMENTS

| | | | |
|---|---|---|---|
| 2,120,702 A | | 6/1938 | Ipatieff et al. |
| 2,456,338 A | * | 12/1948 | Stadtherr ...................... 585/300 |
| 3,137,739 A | * | 6/1964 | Paulis et al. .................. 585/302 |
| 4,123,471 A | * | 10/1978 | Bertolini et al. .............. 585/514 |
| 4,393,259 A | | 7/1983 | Ward et al. |
| 4,777,316 A | | 10/1988 | Harandi et al. |
| 5,659,096 A | | 8/1997 | Randolph et al. |
| 5,811,608 A | | 9/1998 | Stine et al. |
| 5,895,830 A | | 4/1999 | Stine et al. |
| 6,080,903 A | * | 6/2000 | Stine et al. .................... 585/514 |
| 6,107,526 A | | 8/2000 | Frey et al. |
| 6,111,159 A | | 8/2000 | Huff et al. |
| 6,291,734 B1 | * | 9/2001 | Stork ............................ 585/809 |
| 6,548,721 B1 | | 4/2003 | McCulloch et al. |
| 6,590,132 B1 | | 7/2003 | Vora |

(Continued)

FOREIGN PATENT DOCUMENTS

WO 2004072006 A1 8/2004

OTHER PUBLICATIONS

Barker, et al., "Petroleum" in Kirk-Othmer Encyclopedia of Chemical Technology, John Wiley & Sons, 2001, available on-line May 13, 2005.*

(Continued)

Primary Examiner — In Suk Bullock
Assistant Examiner — Bradley Etherton
(74) Attorney, Agent, or Firm — Maryann Maas (57) ABSTRACT

One exemplary embodiment is a process for oligomerizing one or more hydrocarbons. The process includes providing a feed including one or more C3 and C4 hydrocarbons to a separation zone, separating a first stream including an effective amount of C3 olefins for oligomerizing, separating a second stream including an effective amount of one or more C4 olefins for oligomerizing, providing at least a portion of the first stream to a first oligomerization zone for producing at least one of a C9 and a C12 hydrocarbon, and providing at least a portion of the second stream to a second oligomerization zone for producing at least one of a C8 and a C12 hydrocarbon.

18 Claims, 4 Drawing Sheets

(56) References Cited

U.S. PATENT DOCUMENTS

| | | | |
|---|---|---|---|
| 6,689,927 | B1 | 2/2004 | Frame et al. |
| 6,726,834 | B2* | 4/2004 | Quesada et al. ......... 208/120.01 |
| 6,875,900 | B2* | 4/2005 | Koves ........................... 585/510 |
| 6,911,505 | B2 | 6/2005 | Small |
| 6,927,314 | B1 | 8/2005 | Schultz et al. |
| 6,930,206 | B1 | 8/2005 | Groten et al. |
| 7,267,746 | B1 | 9/2007 | Harris et al. |
| 7,396,966 | B2 | 7/2008 | Glover et al. |
| 7,601,309 | B2 | 10/2009 | Krupa et al. |
| 7,678,953 | B2 | 3/2010 | Kuechler et al. |
| 2001/0004972 | A1* | 6/2001 | Miller et al. .................... 208/18 |
| 2006/0194999 | A1* | 8/2006 | Brown et al. ................. 585/467 |
| 2009/0182183 | A1 | 7/2009 | Keenan et al. |
| 2009/0221862 | A1 | 9/2009 | Beadle et al. |

OTHER PUBLICATIONS

Kaibel, "Distillation: Dividing Wall Columns" in Encyclopedia of Separation Science, Academic Press, 2007, I. D. Wilson, ed.—month unknown.*

Cavani, et al., "Effect of Water in the Performance of the 'Solid Phosphoric Acid' Catalyst for Alkylation of Benzene to Cumene and for Oligomerization of Propene" in Applied Catalysis A: General, 97 (1993), 177-196—month unknown.*

Krupa et al., U.S. Appl. No. 12/965,565, filed Dec. 10, 2010, entitled, "Process for Separating at Least One Oligomerized Effluent".

Krupa et al., U.S. Appl. No. 12/965,596, filed Dec. 10, 2010, entitled, "Apparatus and Process for Oligomerizing One or More Hydrocarbons".

* cited by examiner

PROCESS AND APPARATUS FOR OLIGOMERIZING ONE OR MORE HYDROCARBONS

FIELD OF THE INVENTION

This invention generally relates to a process and/or an apparatus for oligomerizing one or more hydrocarbons.

DESCRIPTION OF THE RELATED ART

Often, a feed, including one or more C3 and C4 hydrocarbons, is processed to produce an olefinic alkylate product. Typically, the greater the amount of C4 hydrocarbons in the feed produces a better quality product for gasoline blending due to increased yield of higher octane C8 hydrocarbons and reduced yield of lower octane one or more $C7^-$ hydrocarbons. However, a customer may require complete or partial hydrogenation of the gasoline to meet an olefin specification, and a significant octane penalty may occur due to the poor octane performance of C7, C9, and/or C10 paraffins formed, e.g., via reactions of propene and subsequent hydrogenation. As a result, a gasoline of unsatisfactory octane may be obtained. This reduced octane product can be less attractive for gasoline blending, and possibly even unacceptable.

In addition, the feed may include unacceptable levels of nitriles or other basic organic nitrogen species that require removal. Such nitriles or other nitrogen species can deactivate an acidic oligomerization reactor catalyst and shorten catalyst life. Thus, there is a desire to provide a mechanism to remove one or more nitriles from the feed prior to oligomerization.

Moreover, a unit processing a mixed C3/C4 feed typically makes a poorer quality product. The oligomerized C3 derived products may be difficult to segregate and may not be excluded from hydrogenation, which then can lead to degradation of product octane.

What is more, efficient separation of various hydrocarbon products can minimize the processing of streams in downstream units, such as hydrotreaters. Thus, a scheme that efficiently utilizes equipment can minimize these costs and improve unit operations. As a consequence, generally there is a desire to provide a gasoline manufacturing apparatus that efficiently and effectively produces high quality octane gasoline.

SUMMARY OF THE INVENTION

One exemplary embodiment can be a process for oligomerizing one or more hydrocarbons. Usually, the process includes providing a feed including one or more C3 and C4 hydrocarbons to a separation zone, separating a first stream including an effective amount of C3 olefins for oligomerizing, separating a second stream including an effective amount of one or more C4 olefins for oligomerizing, providing at least a portion of the first stream to a first oligomerization zone for producing at least one of a C9 and a C12 hydrocarbon, and providing at least a portion of the second stream to a second oligomerization zone for producing at least one of a C8 and a C12 hydrocarbon.

Another exemplary embodiment may be an apparatus for oligomerizing one or more hydrocarbons. The apparatus can include a separation zone providing a first stream including an effective amount of C3 olefins for oligomerizing and a second stream including an effective amount of one or more C4 olefins for oligomerizing, a first oligomerization zone adapted to receive at least a portion of the first stream and produces a stream including at least one of a C9 and a C12 olefin, and a second oligomerization zone adapted to receive at least a portion of the second stream and produces another stream including at least one of a C8 and a C12 olefin.

Yet another exemplary embodiment can be a process for oligomerizing one or more hydrocarbons. The process can include providing a feed including one or more C3 and C4 hydrocarbons to a divided wall column, separating a first stream including an effective amount of C3 olefins for oligomerizing, separating a second stream including an effective amount of one or more C4 olefins for oligomerizing, providing at least a portion of the first stream to a first oligomerization zone for producing at least one of a C9 and a C12 hydrocarbon, and providing at least a portion of the second stream to a second oligomerization zone for producing at least one of a C8 and a C12 hydrocarbon.

The embodiments disclosed herein can provide a separation zone for providing a stream substantially including one or more C3 hydrocarbons and a stream substantially including one or more C4 hydrocarbons. Each stream can be processed by a respective oligomerization zone for producing, respectively, one or more C9 and/or C12 hydrocarbons and one or more C8 and/or C12 hydrocarbons, typically olefinic hydrocarbons. In such a manner, the C4 hydrocarbons can be isolated and processed to produce C8 and C12 hydrocarbons that can be utilized for, e.g., a gasoline alkylate or for subsequent processing. In addition, the embodiments disclosed herein can provide a separation zone receiving at least one or more C9 hydrocarbons and one or more C12 hydrocarbons produced from an oligomerization zone. Desirably, the separation zone includes a divided wall column that can efficiently separate the various hydrocarbons into lower chain hydrocarbons for subsequent recycling, C8 hydrocarbons for producing higher quality alkylate, and C12 hydrocarbons for subsequent processing. In addition, a C9 oligomer product can be separated for utilization separate from the C8 rich alkylate.

Additionally, it is desirable to use a water wash vessel to remove any nitrile or other basic nitrogen compounds that can affect downstream oligomerization zones. What is more, the embodiments disclosed herein can provide an oligomerization zone receiving a feed from a separation zone. Desirably, the separation zone is a distillation column. As a result, the oligomerization zone can process the lower chain hydrocarbons in the overhead stream and return longer-chain hydrocarbon reaction-products back to the distillation column. The distillation column can then separate the oligomerized product and provide it for subsequent downstream processing. Desirably, a divided wall column is utilized to efficiently and effectively reduce the operating costs of the apparatus. As such, the embodiments disclosed herein can provide an efficient apparatus for separating and processing a feed including one or more C3 and C4 hydrocarbons.

DEFINITIONS

As used herein, the term "stream" can include various hydrocarbon molecules, such as straight-chain, branched, or cyclic alkanes, alkenes, alkadienes, and alkynes, and optionally other substances, such as gases, e.g., hydrogen, or impurities, such as heavy metals, and sulfur and nitrogen compounds. The stream can also include aromatic and non-aromatic hydrocarbons. Moreover, the hydrocarbon molecules may be abbreviated C1, C2, C3 ... Cn where "n" represents the number of carbon atoms in the one or more hydrocarbon molecules. Furthermore, a superscript "+" or "−" may be used with an abbreviated one or more hydrocarbons notation, e.g., $C3^+$ or $C3^-$, which is inclusive of the abbreviated one or more hydrocarbons. As an example, the abbreviation "C3+" means one or more hydrocarbon molecules of three carbon atoms and/or more.

As used herein, the term "zone" can refer to an area including one or more equipment items and/or one or more sub-zones. Equipment items can include one or more reactors or reactor vessels, heaters, exchangers, pipes, pumps, compressors, and controllers. Additionally, an equipment item, such as a reactor, dryer, or vessel, can further include one or more zones or sub-zones.

As used herein, the term "rich" can mean an amount of at least generally about 30%, preferably about 50%, and optimally about 70%, by weight, of a compound or class of compounds in a stream.

As used herein, the term "substantially" can mean an amount of at least generally about 80%, preferably about 90%, and optimally about 99%, by weight, of a compound or class of compounds in a stream.

As used herein, the term "fractionated recycle circuit" can include at least one stream, typically an overhead stream, withdrawn from a column, typically a distillation column, and passed through at least one reaction zone, where at least a portion of the reaction zone effluent is returned to the column.

As used herein, the term "overhead stream" can mean a stream withdrawn at or near a top of a column, typically a distillation column.

As used herein, the term "bottom stream" can mean a stream withdrawn at or near a bottom of a column, typically a distillation column.

As used herein, the terms "paraffin" and "alkane" may be used interchangeably.

As used herein, the terms "olefin" and "alkene" may be used interchangeably.

As used herein, the term "isooctane" may refer to 2,2,4-trimethylpentane.

As used herein, the term "isooctene" may refer to a mixture of isomers of trimethylpentenes.

As used herein, the term "vapor" can mean a gas or a dispersion that may include or consist of one or more hydrocarbons and have liquid, gas, and/or solid phases.

As used herein, the terms, e.g., "part", "portion", "feed", "effluent", "product", "stream", and "line" may be used interchangeably when referring to the process flow lines in the drawings.

DETAILED DESCRIPTION

Figure 1:
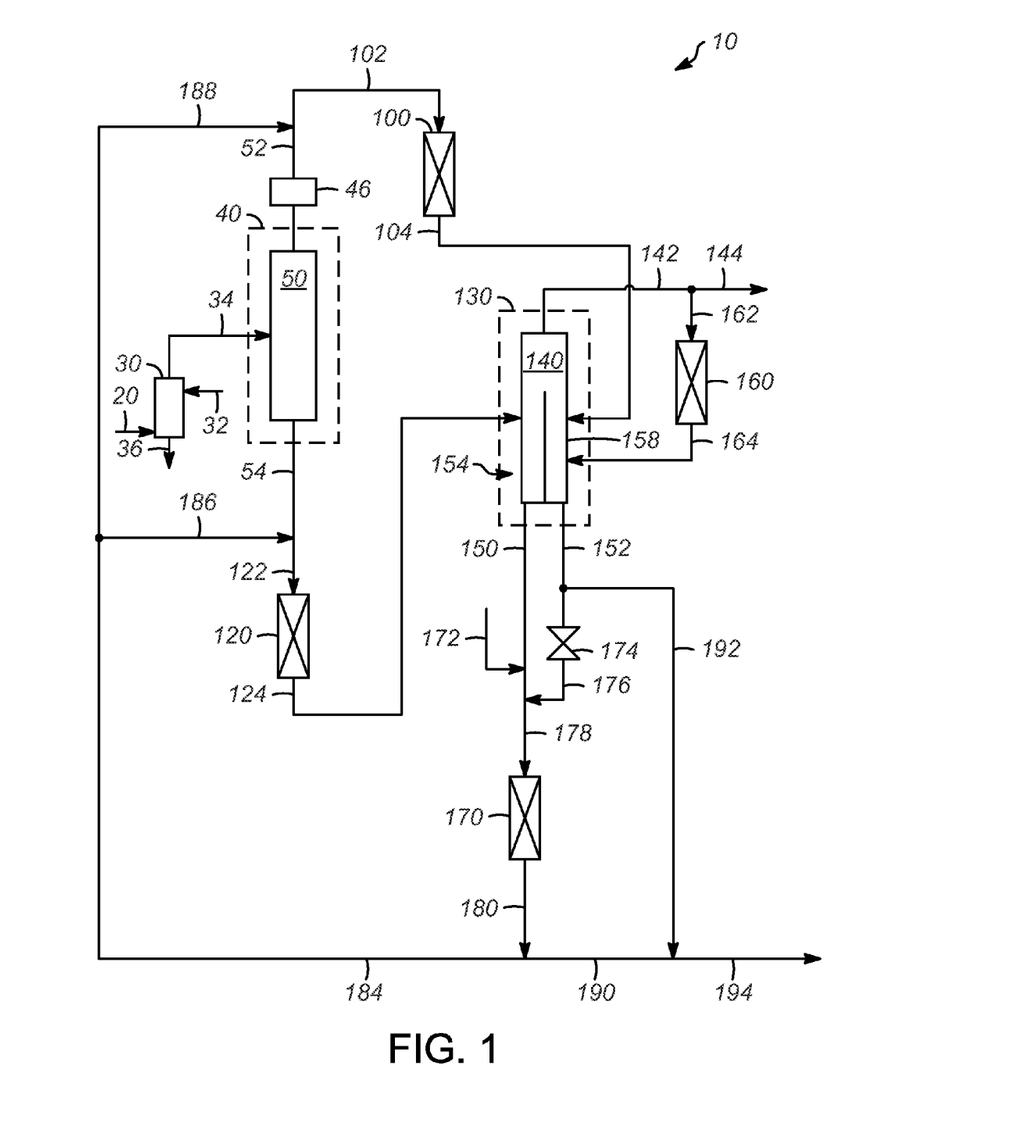
FIG. 1 is a schematic depiction of an exemplary apparatus.

Referring to FIG. 1, one exemplary apparatus 10 is depicted for producing a gasoline product that can include a water wash zone 30; a first separation zone 40; a first oligomerization zone 100, preferably a C3 oligomerization zone; a second oligomerization zone 120, preferably a C4 oligomerization zone; a second separation zone 130; a third oligomerization zone 160; and a hydrotreatment zone 170.

The water wash zone 30, which may be upstream of the first separation zone 40, can include a vessel that can receive a feed 20 including one or more C3 and C4 hydrocarbons. Typically, the feed 20 can include at least about 90%, by weight, preferably about 99%, by weight, of one or more C3 and C4 hydrocarbons. The water wash zone 30 can receive a wash stream 32, typically water, to wash the incoming feed 20 to remove one or more nitrile compounds and/or other basic organic nitrogen species to a level effective to minimize the effect on downstream oligomerization zones. A wash effluent 36 can exit the water wash zone 30 approximately at a bottom of a wash vessel while a washed feed 34 can exit the water wash zone 30 and proceed to the first separation zone 40.

The first separation zone 40 can include any suitable separation device, such as a distillation column 50. The distillation column 50 can provide a split between the C3 and C4 hydrocarbons. Generally, the C3 and C4 hydrocarbons include a large percentage of olefins. Although reflux and reboiling streams are not depicted, it should be understood that such a distillation column 50 would typically include these streams as well as associated equipment, such as a receiver and a reboiler. A first or overhead stream 52 including an effective amount of C3 olefins, such as propene, for oligomerization can be combined with a portion 188 of a recycle stream 184, as hereinafter described. Typically, the first stream 52 can include about 10-about 90%, by weight, of C3 olefins based on the weight of the first stream 52. The first stream 52 can be passed through a drying zone 46 to reduce the water in the stream 52 prior to being combined with the portion 188 to form a combined feed 102 for the first oligomerization zone 100. Alternatively, the drying zone 46 may be omitted or positioned downstream to dry the combined feed 102.

The first oligomerization zone 100 can be any suitable reaction zone that can oligomerize the propene to larger chain olefins, such as C6, C9, and C12 olefins. Although the first oligomerization zone 100 may be referred to as a C3 oligomerization zone 100, it should be understood that other olefins may be oligomerized as well. The first oligomerization zone 100 can include a reactor for conducting an oligomerization reaction. The reactor can contain any suitable catalyst, typically an acid catalyst such as a zeolite or at least one of a solid phosphoric acid and sulfonic acid ion exchange resin catalyst, as disclosed in, e.g., U.S. Pat. No. 7,601,309 and US 2009/0221862 A1. Typically, the first oligomerization zone 100 can operate at a temperature of about 70-about 300° C. or even about 70-about 150° C., and a pressure of about 1,200-about 8,375 kPa. The reaction may be in a vapor phase, such as a gas phase, or a liquid phase. Typically, the first oligomerization zone 100 can have a selectivity for C9 olefins of about 50-about 55%, by weight, and a selectivity for C12 olefins of about 25-about 30%, by weight, based on the weight of the one or more olefins converted to oligomer in the combined feed 102. An effluent 104, which may be a first effluent, can be provided to the second separation zone 130. Generally, the effluent 104 can include one or more C9 olefins. Exemplary oligomerization zones are disclosed in, e.g., U.S. Pat. No. 7,601,309 and US 2009/0221862 A1.

A second or bottom stream 54 can be combined with a portion 186 of a recycle stream 184, as hereinafter described, to form a combined feed 122 for the second oligomerization zone 120. Generally, splitting the recovery of the C3 and C4 hydrocarbons can separate any water into the overhead stream 52. As a result, the bottom stream 54 can be substantially free of water, which may benefit the catalyst in the second oligomerization zone 120. Usually, the second oligomerization zone 120 contains a reactor for conducting an oligomerization reaction. The reactor can contain any suitable catalyst, typically an acid catalyst, such as a zeolite or at least one of a solid phosphoric acid and sulfonic acid ion exchange resin catalyst, as disclosed in, e.g., U.S. Pat. No.

7,601,309 and US 2009/0221862 A1. Typically, the second oligomerization zone 120 operates at a temperature of about 70-about 300° C. or even about 70-about 150° C., and a pressure of about 1,200-about 8,375 kPa, preferably a pressure that can maintain the reaction in a liquid phase. Generally, the second stream 54 can include an effective amount of one or more C4 olefins for oligomerization, such as about 10-about 90%, by weight, of one or more C4 olefins based on the weight of the second stream 54. Exemplary oligomerization zones are disclosed in, e.g., U.S. Pat. No. 7,601,309 and US 2009/0221862 A1.

The second oligomerization zone 120 can convert the C4 olefins into one or more C8 and C12 hydrocarbons, usually C8 and C12 olefins. Conditions can be tailored so that about 97%, by weight, of the isobutene and about 60%, by weight, of the normal butene in the combined feed 122 can be converted into product olefins, with a product olefin selectivity of at least about 90%, by weight, C8 olefins and no more than about 10%, by weight, C12 olefins based on the weight of the one or more olefins converted to oligomer in the combined feed 122. The effluent 124 from the second oligomerization zone 120 can be provided to the second separation zone 130.

The second separation zone 130 can receive the effluents 104 and 124. Typically, the second separation zone 130 can include a divided wall column 140 containing a dividing wall 158 at least partially comprised in a lower half 154. Exemplary divided wall columns are disclosed in, e.g., U.S. Pat. No. 6,927,314 B1 and U.S. Pat. No. 7,601,309 B2. Generally, the divided wall column 140 can receive at least a portion of a plurality of effluents 104 and 124 on either side of the divided wall column 140. The effluents 104 and 124 can be provided on opposing sides of the divided wall column 140 for producing a first or overhead stream 142 including C3 and C4 hydrocarbons and a second stream or first bottom stream 150 including one or more C8-C12 hydrocarbons, and a third stream or second bottom stream 152 including one or more C9-C12 hydrocarbons. Generally, the divided wall column 140 can operate at any suitable conditions providing a separation between the $C5^-$ hydrocarbons and the $C6^+$ hydrocarbons at the top and the bottom of the divided wall column 140. The overhead stream 142 can be split into a raffinate stream 144 that can be provided to any suitable downstream process and a feed 162 that can be provided to the third oligomerization zone 160, which can include a reactor. The oligomerization reactor can operate at any suitable conditions to oligomerize the C3 and C4 hydrocarbons into one or more $C6^+$ hydrocarbons, and can include any suitable catalyst and may operate at similar conditions as, e.g., first oligomerization zone 100 and the second oligomerization zone 120. An effluent 164 from the third oligomerization zone 160 can be returned to the second separation zone 130 for separation of oligomer products from C3 and C4 paraffins and unconverted C3 and C4 olefins.

The second stream 150 from the second separation zone 130 can be combined with hydrogen from a hydrogen stream 172 to be comprised in a combined feed 178 for the hydrotreatment zone 170. Usually, the conditions in the hydrotreatment zone 170 are sufficient, e.g., temperature and pressure, to saturate the alkenes and substantially convert them to alkanes. One exemplary catalyst can be a noble metal, such as palladium, with the hydrogenation catalyst operated at a temperature of about 20-about 150° C. and a pressure of about 2,000-about 3,500 kPa. An exemplary hydrotreatment zone is disclosed in, e.g., U.S. Pat. No. 6,107,526. As such, an effluent or product stream 180 can include less than about 0.1%, by weight, alkenes, preferably less than about 0.01%, by weight, alkenes.

Optionally, a feed stream 176 including one or more C6-C12 hydrocarbons can be provided from the third stream 152 or a portion thereof by opening a valve 174. The combined feed 178, optionally including a portion of the third stream 152, can be provided to the hydrotreatment zone 170 to convert the olefins into paraffins. The effluent 180 can be at least comprised in a recycle stream 184 that can have the portion 186 provided to the second oligomerization zone 120 and a portion 188 provided to the first oligomerization zone 100. Optionally, another portion of the effluent can be recycled to the inlet of the hydrotreatment zone 170 to control the temperature rise of the exothermic reaction. A split stream 190 can be combined with a product stream 192 having one or more C9-C12 hydrocarbons, preferably olefinic hydrocarbons, from the third stream 152 and form a combined product stream 194.

Figure 2:
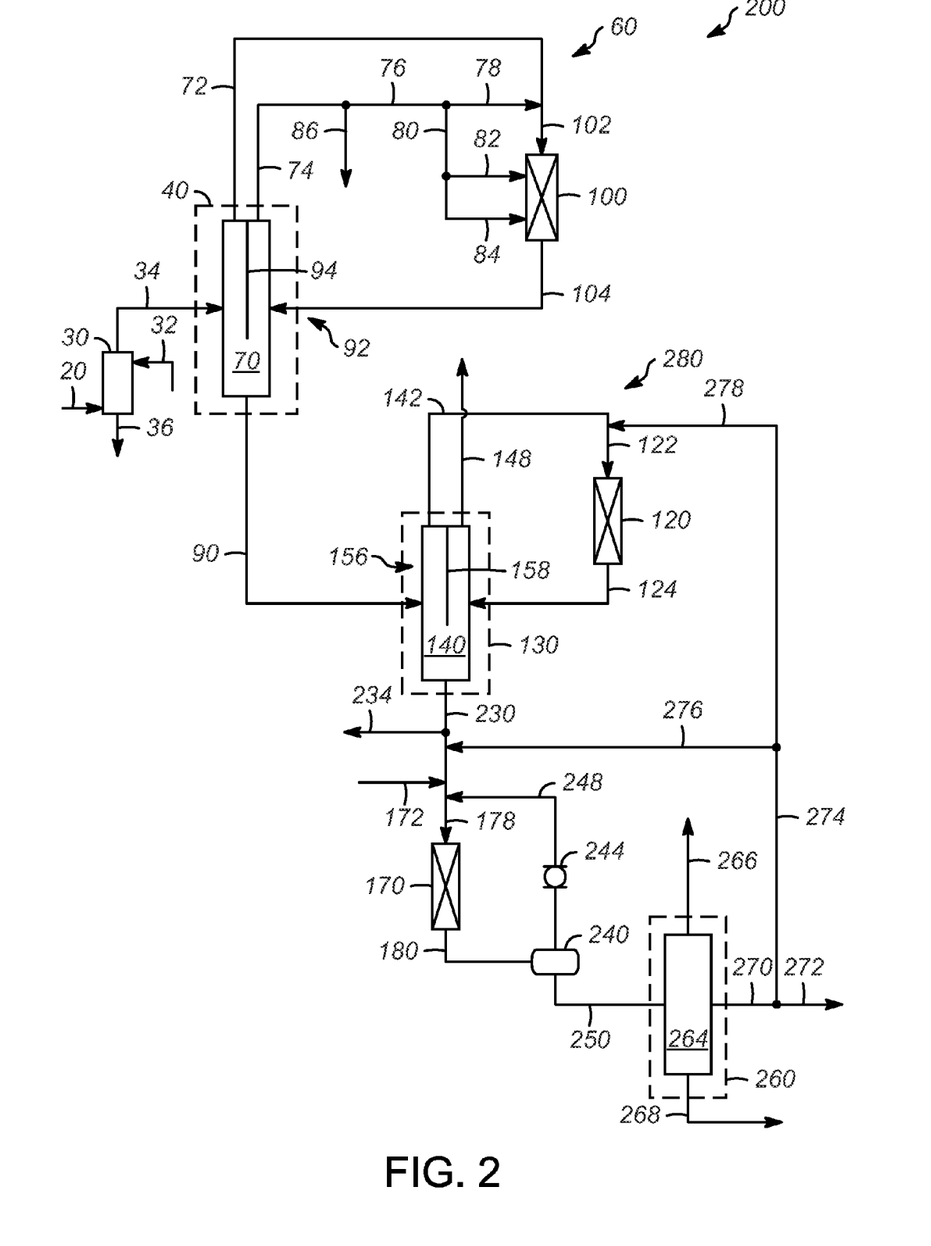
FIG. 2 is a schematic depiction of another exemplary apparatus.

Referring to FIG. 2, another exemplary apparatus 200 is depicted for producing a gasoline product that can include the water wash zone 30, the first separation zone 40, the first oligomerization zone 100, the second oligomerization zone 120, the second separation zone 130, the hydrotreatment zone 170, and a third separation zone 260. Generally, a fractionated recycle circuit 60 may include the first separation zone 40 and the first oligomerization zone 100, and a fractionated recycle circuit 280 may include the second separation zone 130 and the second oligomerization zone 120.

Generally, the feed 20 can be provided to the water wash zone 30 to provide the washed feed 34, and in turn can be provided to the first separation zone 40, as described above for the apparatus 10. In this exemplary embodiment, the first separation zone 40 can include a divided wall column 70. Generally, the divided wall column 70 can include a dividing wall 94 that can be at least partially positioned in an upper half 92 of the divided wall column 70. Exemplary divided wall columns are disclosed in, e.g., U.S. Pat. No. 6,927,314 B1 and U.S. Pat. No. 7,601,309 B2. The divided wall column 70 can provide a first stream or an overhead stream 72 including at least generally about 40%, by weight, propene based on the weight of the first stream 72. In addition, the divided wall column 70 can also provide a second stream 74 of no more than about 10%, by weight, of propene based on the weight of the second stream or second overhead stream 74. Typically, the first stream 72 can be comprised in a combined feed 102 to the first oligomerization zone 100. The second stream 74 can provide a propene depleted product stream 86 with another portion 76 being split yet again. Particularly, the portion 76 can be split into a quench stream 80, which in turn can be split into a first quench portion 82 and a second quench portion 84, although any number of quench streams may be used. The portion 76 can also provide a remainder stream 78 that may be combined with the first stream 72 to form the combined feed 102 to the first oligomerization zone 100. The first oligomerization zone 100 can be similar as described above and provide an effluent 104 that may serve as a recycle to the divided wall column 70. A bottom stream 90 including one or more $C4^+$ hydrocarbons, particularly including one or more C9 and C12 olefins, from the divided wall column 70 can be provided to the second separation zone 130.

The second separation zone 130 can include a divided wall column 140 that may include a dividing wall 158 at least partially positioned in the upper half 156 of the divided wall column 140. The divided wall column 140 can provide a first or overhead stream 142 including one or more C4 hydrocarbons. In addition, the divided wall column 140 may also provide a second overhead stream 148 including one or more C4 hydrocarbons.

The overhead stream 142 can be combined with a second recycle portion 278, as hereinafter described. The combined feed 122 can be provided to the second oligomerization zone 120, which may provide the effluent 124, as described above for the apparatus 10 in FIG. 1. The effluent 124 can serve as a recycle to and be received on at least one side of the divided wall column 140. The bottom stream 230 can include one or more C8, C9 and/or C12 olefins and, optionally, a product stream 234 can be withdrawn. What is more, the remainder can be combined with a first recycle portion 276, as hereinafter described, as well as hydrogen from the hydrogen stream 172, typically make-up hydrogen, and a recycle hydrogen stream 248, as hereinafter described, to form the combined feed 178. The combined feed 178 can be provided to the hydrotreatment zone 170 to provide the hydrotreated effluent 180, as described above for the apparatus 10.

The effluent 180, including one or more C8, C9 and C12 paraffins, can be provided to a product separator 240 that may provide the recycle hydrogen stream 248 with a bottom liquid stream 250 from the product separator 240 being provided to a third separation zone 260. The recycle hydrogen stream 248 can typically be sent to a compressor 244 to sufficiently increase pressure to allow flow into the combined feed 178.

The third separation zone 260 can include a distillation column 264, operating at any suitable pressure and temperature, to provide an overhead stream 266 including hydrogen, hydrogen sulfide and one or more C1-C4 hydrocarbons and a bottom stream 268 including one or more C12 and C16 oligomers. A side-stream 270 from the distillation column 264 can provide a product stream 272 including one or more C8, C9 and/or C12 hydrocarbons, usually iso-hydrocarbons. This product stream 272 can be provided to a gasoline blending pool. A recycle stream 274 including the first recycle portion 276 and the second recycle portion 278 can be split from the side-stream 270 and provided, respectively, to the second oligomerization zone 120 and the hydrotreatment zone 170.

Figure 3:
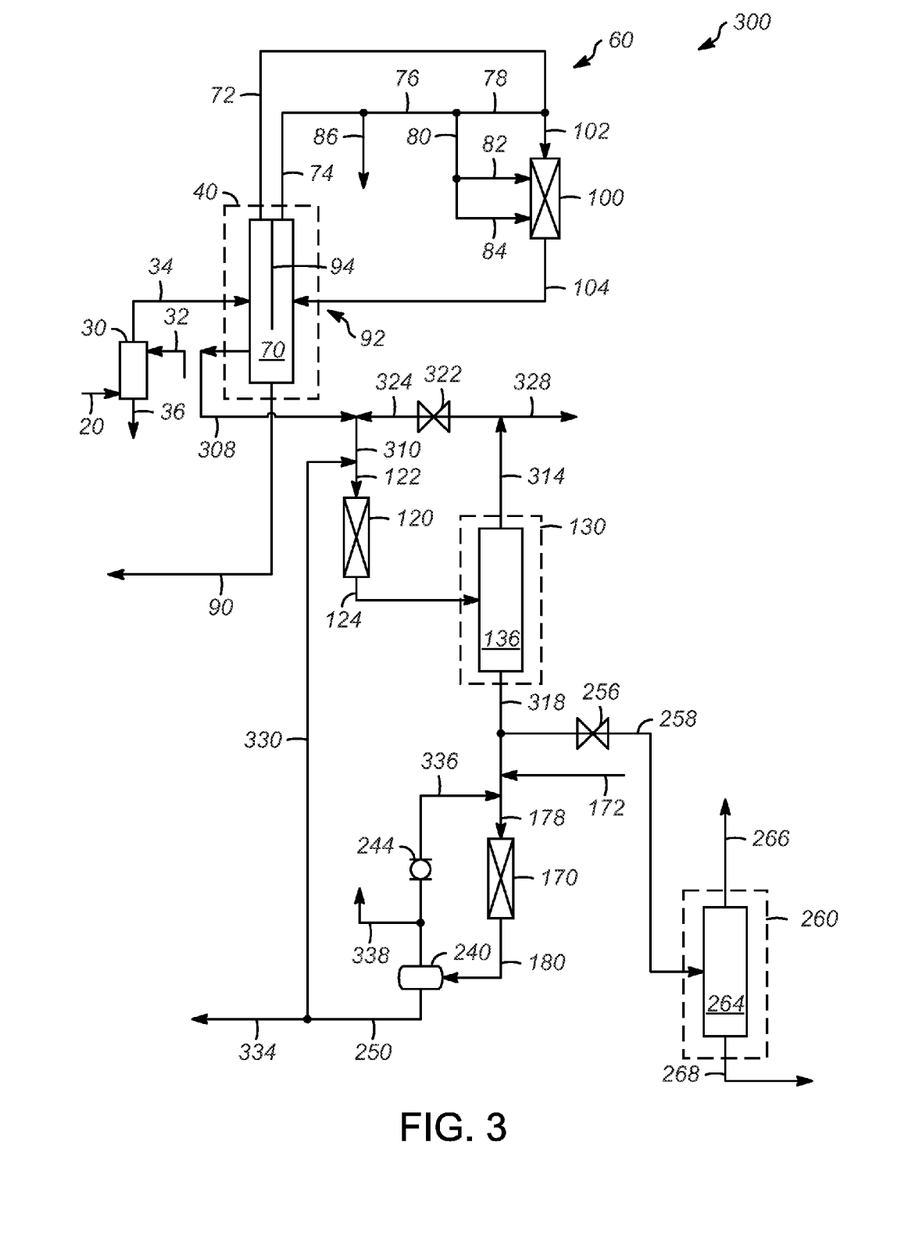
FIG. 3 is a schematic depiction of a further exemplary apparatus.

Referring to FIG. 3, a further exemplary embodiment of an apparatus 300 for producing a gasoline product is depicted. The apparatus 300 can include the water wash zone 30, the fractionated recycle circuit 60, the first separation zone 40, the first oligomerization zone 100, the second oligomerization zone 120, the second separation zone 130, the hydrotreatment zone 170, and the third separation zone 260.

In this exemplary apparatus, the water wash zone 30 and the fractionated recycle circuit 60, including the first separation zone 40 and the first oligomerization zone 100, can be substantially the same as described above for the apparatus 200. However, a side-stream 308 including one or more C4 olefins, can be pulled from the divided wall column 70 in addition to producing the bottom stream 90. In this instance, the bottom stream 90 can include one or more C6+ hydrocarbons, such as C9 and/or C12 iso-olefins. Particularly, the oligomerized propene product, namely C9 and C12 olefins, in the effluent 104 from the first oligomerization zone 100, can be recycled to the divided wall column 70. In the divided wall column 70, the C9 and C12 olefins may be withdrawn via the bottom stream 90 and used for other processes or for blending into the gasoline pool. Optionally, part of the bottom stream 90 may be sent to the third separation zone 260 for removing one or more C12+ hydrocarbons, such as olefinic hydrocarbons.

The side-stream 308 can be provided to the second oligomerization zone 120 as a portion 310 of the combined feed 122. Particularly, a part 324 of an overhead stream 314, as hereinafter described, can optionally pass through a valve 322, if open, to be combined with the side-stream 308. The streams 308 and 324 can be combined with a part 330 of a bottom liquid stream 250, as hereinafter described, to be comprised in the combined feed 122. The effluent 124 can be provided to the second separation zone 130.

The effluent 124 may contain oligomerized C4 olefins, typically C8 and C12 hydrocarbons. The effluent 124 can then be provided to the second separation zone 130. The second separation zone 130 can include a distillation column 136 providing an overhead stream 314 that can include C4− hydrocarbons that can pass from the unit to be used in other processes as a stream 328. Optionally, a portion of the stream can be combined as the part 324 with the side-stream 308. A second or bottom stream 318 including C8+ hydrocarbons, typically one or more C8 and C12 hydrocarbons, can be combined with hydrogen from the hydrogen stream 172 and another portion 336, as hereinafter described, to form the combined feed 178 to the hydrotreatment zone 170. The hydrotreatment zone 170 can saturate the olefins to provide a paraffinic product as an effluent 180 which can be provided to the product separator 240. Excess hydrogen gas can leave the product separator 240 and pass out as a purge stream 338 including hydrogen, water, hydrogen sulfide, and one or more C1-C4 hydrocarbons with another portion 336 recycled to be combined with the bottom stream 318 via the compressor 244. A bottom liquid stream 250 from the product separator 240 can be split into a product stream 334 including one or more C8+ hydrocarbons, such as one or more C8 and/or C12 iso-hydrocarbons that can be sent for downstream processing or for use in the gasoline blending pool. In particular, the heavier iso-paraffins, i.e., C12+ hydrocarbons, can be separated from the C8 and C9 hydrocarbons in subsequent downstream fractionation. The part 330 of the bottom liquid stream 250 can also be recycled to be comprised in the combined feed 122 for the second oligomerization zone 120.

Optionally, a valve 256 can be opened to provide at least a portion of the bottom stream 318 as a stream 258 to the third separation zone 260. The third separation zone 260, as described above, can include the distillation column 264. Optionally, this distillation column 264 can be used to separate an overhead stream 266 rich in C8 and C9 olefins and paraffins, and depleted in C12+ hydrocarbons from the bottom stream 268 rich in C12+ hydrocarbons. Particularly, the overhead stream 266 can include iso-octane, iso-octene, and/or C9 hydrocarbons, while the bottom stream 268 can provide C8+ hydrocarbons that are rich in C12 hydrocarbons. Thus the third separation zone 260 can separate the products suitable for the gasoline blending pool, namely C8 and C9 hydrocarbons, from the heavier hydrocarbons, namely C12+ hydrocarbons that are less desirable as gasoline blending components.

Figure 4:
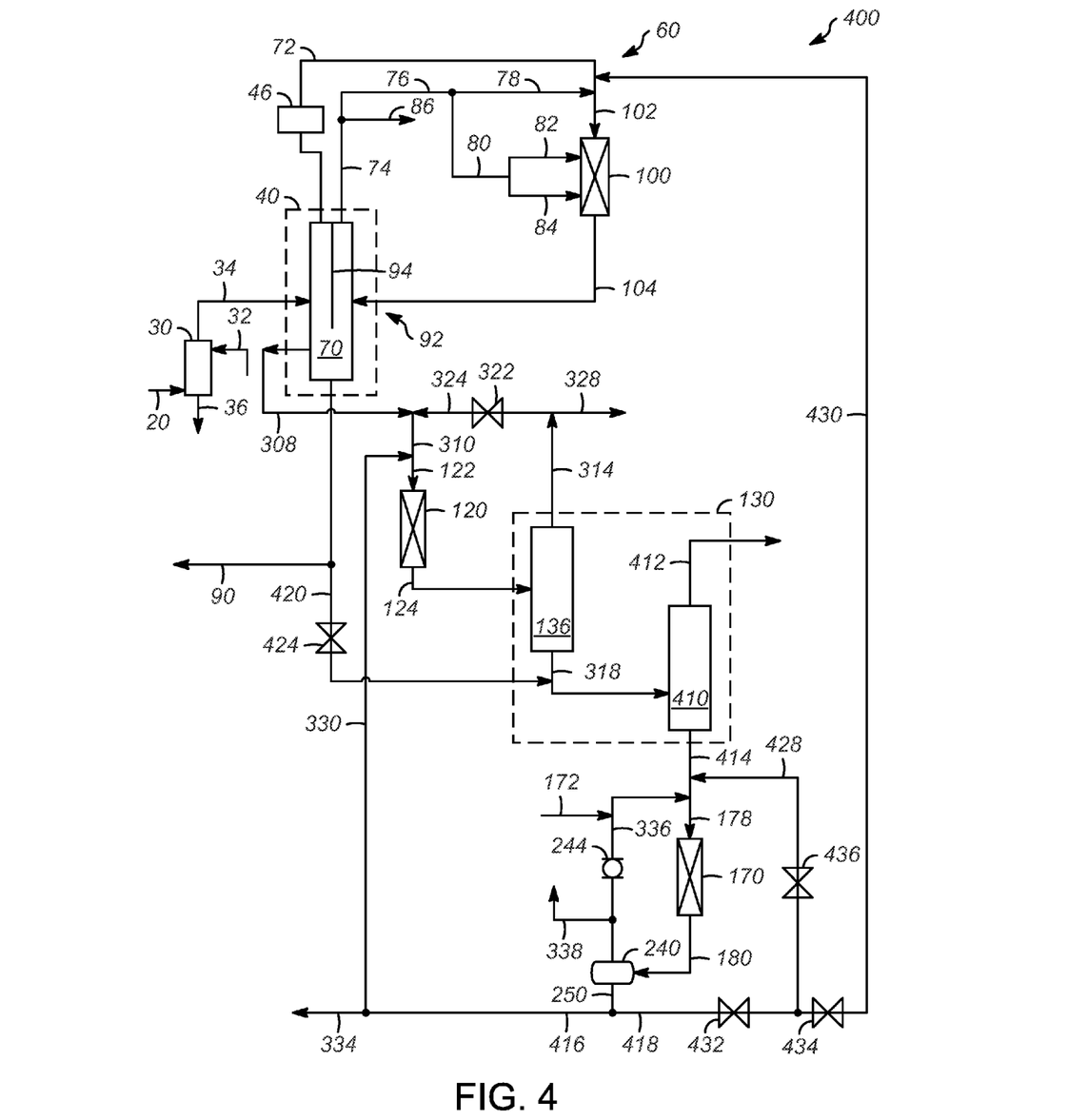
FIG. 4 is a schematic depiction of yet another exemplary apparatus.

Referring to FIG. 4, yet another exemplary apparatus 400 for producing a gasoline product is depicted. This exemplary apparatus 400 can be operated in two different modes, as hereinafter described. Generally, the apparatus 400 can include the water wash zone 30, the first separation zone 40, the fractionated recycle circuit 60 including the first oligomerization zone 100, the second oligomerization zone 120, the second separation zone 130, and the hydrotreatment zone 170.

The water wash zone 30, the first separation zone 40 and the fractionated recycle circuit 60 can be substantially the same as described above for the apparatus 300 in FIG. 3, except that the first or overhead stream 72 can pass through the drying zone 46, as described above. Generally, the effluent 104 from the first oligomerization zone 100 can have a selectivity of about 60-about 75%, by weight, C9 olefins, and about 10-about 15%, by weight, C12 olefins based on the weight of the one or more olefins converted to oligomer in the combined feed 102, as a result of recycling a stream 430, as hereinafter described. Otherwise, the zones 30, 40, and 100 can operate substantially the same as described above. The side-stream 308 can be withdrawn from the first separation zone 40 and optionally combined with the part 324 of the first or overhead stream 314 from the second separation zone 130 to be comprised in the combined feed 122 for the second oligomerization zone 120, as described above. The combined feed 122 may also include the part 330 of the bottom liquid stream 250, as described above. The combined feed 122 can be provided to the second oligomerization zone 120 to provide one or more C8 and C12 hydrocarbons. The effluent 124 can be provided to the second separation zone 130.

The bottom stream 90 from the first separation zone 40 can be recovered as a product with a valve 424 closed and can include one or more C6+ hydrocarbons, such as C9 and C12 iso-olefins. Alternatively, the valve 424 can be opened and a stream 420, including a part or all of the bottom stream 90, can be provided to the second separation zone 130 for further processing. The second separation zone 130 can include the distillation column 136, which can be a first distillation column, and a distillation column 410, which can be a second distillation column.

The distillation column 136 can provide the overhead stream 314 that can be provided as a product stream 328 including one or more C4 hydrocarbons. In addition, the valve 322 can be opened to provide at least a part 324 of this overhead stream 314 as a recycle to be combined with the side-stream 308 for further processing through the second oligomerization zone 120.

The bottom stream 318, optionally including a part of the bottom stream 90 of the first separation zone 40, can be provided to the distillation column 410. The distillation column 410 can provide an overhead stream 412 including one or more iso-olefins, namely C8 and C12 iso-olefins, as well as one or more C8 and C12 iso-paraffins. Typically, this material can be provided to the blending pool and can reduce the size of the hydrotreatment zone 170 by removing this material from the second separation zone 130.

A bottom stream 414 can be removed from the second separation zone 130, and optionally, with the stream 428 that can receive hydrogen from both streams 172 and 336, as hereinafter described, comprise the combined feed 178. Particularly, the combined feed 178 can be provided to the hydrotreatment zone 170 to provide a paraffinic product that can be removed as the effluent 180 and provided to the product separator 240. Typically, one or more C1-C4 hydrocarbons, as well as water, hydrogen, and hydrogen sulfide, can be removed as a purge stream 338 with the remainder passing through the compressor 244. The stream 336, including substantially hydrogen, can be combined with the make-up hydrogen stream 172 and be provided with the hydrocarbons entering as the combined feed 178 to the hydrotreatment zone 170.

The product separator 240 may also provide a bottom liquid stream 250 that can be split into streams 416 and 418. Optionally, the stream 416 can provide a product stream having one or more C12 and C16 iso-paraffins with the part 330 being recycled to the second oligomerization zone 120. The stream 418 can pass through a valve 432 and a valve 436 with a valve 434 closed as a recycle stream 428 to be combined with the bottom stream 414 of the second separation zone 130. These combined streams 428 and 414 after being added with hydrogen can then be provided to the hydrotreatment zone 170, as described above. Alternatively, a portion of the stream 418 can pass through the valve 432 and also the valve 434 to form the stream 430 recycled to the first oligomerization zone 100 by being combined with the first stream 72 of the fractionated recycle circuit 60. Thus, the stream 418 may be split into the streams 428 and 430. Usually, the stream 418 can include primarily one or more paraffinic compounds, such as C12 and C16 iso-hydrocarbons as well as olefinic C12 and C16 iso-hydrocarbons.

In this exemplary embodiment of the apparatus 400, the provision of the distillation column 410 can separate lighter hydrocarbons prior to hydrogenation, thus lessening the duty requirements of the hydrotreatment zone 170 and associated equipment, such as recycle gas compressors and distillation columns. Further flexibility may be provided by opening the valve 424 to provide additional paraffinic material, after subsequent hydrogenation in the hydrotreatment zone 170, to offset losses of hydrogenated products from the apparatus 400 via the bottom stream 90. Optionally, the first oligomerization zone 100 may be conducted in a liquid phase to improve catalyst life. As such, a C12 iso-paraffin solvent can be recycled to the first oligomerization zone 100.

Generally, the embodiments disclosed herein allow the separate processing of C3 and C4 hydrocarbons to produce olefinic C8, C9, C12, and C16 hydrocarbons that can be subsequently separated and optionally hydrotreated to provide a C8 hydrocarbon product as well as other oligomer compounds that can be utilized in downstream operations. Moreover, the gasoline product can have a low olefinic concentration to meet regulatory requirements. Thus, the embodiments disclosed herein can provide a high quality and efficient process for producing gasoline alkylate. Moreover, the oligomerized products, e.g., C8 and C12 oligomer products can be used in intermediates and final products for one or more detergents, plasticizers, and lubricants.

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

In the foregoing, all temperatures are set forth in degrees Celsius and, all parts and percentages are by weight, unless otherwise indicated.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. A process for oligomerizing one or more hydrocarbons, comprising:
A) providing a washed feed comprising one or more C3 and C4 hydrocarbons to a first separation zone, wherein the washed feed comprising one or more C3 and C4 hydrocarbons has been waterwashed to remove one or more nitrile compounds;
B) separating, via the first separation zone, a first stream comprising an effective amount of C3 olefins for oligomerizing;
C) drying at least a portion of the first stream to reduce water in the first stream and producing a dried first stream;
D) separating, via the first separation zone, a second stream comprising an effective amount of one or more C4 olefins for oligomerizing, wherein the second stream is substantially free of water;
E) providing at least a portion of the dried first stream to a first oligomerization zone for producing a first effluent stream comprising both a C9 hydrocarbon and a C12 hydrocarbon;

F) providing at least a portion of the second stream to a second oligomerization zone for producing a second effluent stream comprising both a C8 hydrocarbon and a C12 hydrocarbon, wherein the second effluent stream is a separate stream from the first effluent;

G) providing at least a portion of the first effluent stream and at least a portion of the second effluent stream to a second separation zone; and H) separating, via the second separation zone, into at least one stream comprising one or more C8, C9 and C12 hydrocarbons.

2. The process according to claim 1, wherein the first oligomerization zone comprises at least one acid catalyst.

3. The process according to claim 2, wherein the first oligomerization zone is at a temperature of about 70-about 300° C. and a pressure of about 1,200-about 8,375 kPa.

4. The process according to claim 1, wherein the second oligomerization zone comprises at least one acid catalyst.

5. The process according to claim 1, wherein the second oligomerization zone operates at a temperature of about 70-about 300° C. and a pressure of about 1,200-about 8,375 kPa.

6. The process according to claim 1, wherein the second oligomerization zone comprises a solid phosphoric acid catalyst and operates at a temperature of about 70-about 300° C. and at a pressure of about 1,200-about 8,375 kPa.

7. The process according to claim 1, wherein the second oligomerization zone comprises a sulfonic acid ion exchange resin catalyst and operates at a temperature of about 70-about 150° C. and at a pressure of about 1,200-about 8,375 kPa.

8. The process according to claim 1, wherein the first stream comprises about 10-about 90%, by weight, of C3 olefins based on the weight of the first stream.

9. The process according to claim 1, wherein the second stream comprises about 10-about 90%, by weight, of one or more C4 olefins based on the weight of the second stream.

10. The process according to claim 1, wherein the first separation zone comprises a distillation column providing an overhead stream comprising the first stream and a bottom stream comprising the second stream.

11. The process according to claim 1, wherein the first separation zone comprises a divided wall column.

12. The process according to claim 11, wherein the divided wall column provides a side-stream comprising the second stream.

13. The process according to claim 11, wherein the divided wall column provides a bottom stream comprising the second stream.

14. A process for oligomerizing one or more hydrocarbons, comprising:
A) providing a washed feed comprising one or more C3 and C4 hydrocarbons to a separation zone, wherein the washed feed comprising one or more C3 and C4 hydrocarbons has been waterwashed to remove one or more nitrile compounds;
B) separating a first stream comprising an effective amount of C3 olefins for oligomerizing;
C) separating a second stream comprising an effective amount of one or more C4 olefins for oligomerizing, wherein the second stream is substantially free of water;
D) providing at least a portion of the first stream to a first oligomerization zone for producing a first effluent stream comprising both a C9 hydrocarbon and a C12 hydrocarbon, wherein the at least a portion of the first stream provided to the first oligomerization zone is dried to form a dried first stream prior to being provided to the first oligomerization zone; and
E) providing at least a portion of the second stream to a second oligomerization zone for producing a second effluent stream comprising both a C8 hydrocarbon and a C12 hydrocarbon, wherein the second effluent stream is a separate stream from the first effluent stream;
F) recycling at least a portion of the at least one of a C8 and a C12 hydrocarbon produced in the second oligomerization zone, after being combined with hydrogen in a hydrotreatment zone, to the first oligomerization zone.

15. The process of claim 14 further comprising drying the at least a portion of the first stream to a first oligomerization zone and the recycled at least a portion of the at least one of a C8 and a C12 hydrocarbon produced in the second oligomerization zone prior to providing to the first oligomerization zone.

16. The process of claim 14 further comprising recycling at least a portion of the at least one of a C8 and a C12 hydrocarbon produced in the second oligomerization zone, after being combined with hydrogen in a hydrotreatment zone, to the second oligomerization zone.

17. The process of claim 14 further comprising recycling at least a portion of the at least one of a C9 and a C12 hydrocarbon produced in the first oligomerization zone, after being combined with hydrogen in a hydrotreatment zone, to the first oligomerization zone, the second oligomerization zone, or both.

18. A process for oligomerizing one or more hydrocarbons, comprising:
A) providing a washed feed comprising one or more C3 and C4 hydrocarbons to a separation zone, wherein the washed feed comprising one or more C3 and C4 hydrocarbons has been waterwashed to remove one or more nitrile compounds;
B) separating, within a first separation zone, a first stream comprising an effective amount of C3 olefins for oligomerizing;
C) separating, within the first separation zone, a second stream comprising an effective amount of one or more C4 olefins for oligomerizing, wherein the second stream is substantially free of water;
D) providing at least a portion of the first stream to a first oligomerization zone for producing a first effluent stream comprising both a C9 hydrocarbon and a C12 hydrocarbon, wherein the at least a portion of the first stream provided to the first oligomerization zone is dried to form a dried first stream prior to being provided to the first oligomerization zone; and
E) providing at least a portion of the second stream to a second oligomerization zone for producing a second effluent stream comprising both a C8 hydrocarbon and a C12 hydrocarbon, wherein the second effluent stream is a separate stream from the first effluent stream;
F) separating the C8 hydrocarbon and the C12 hydrocarbon from the second oligomerization zone into a C8 product stream and a C12 stream;
G) collecting the C8 product stream and recycling at least a portion of the C12 stream, after being combined with hydrogen in a hydrotreatment zone, to the first oligomerization zone, the second oligomerization zone, or both.

* * * * *